(12) United States Patent
McCloud

(10) Patent No.: US 8,181,918 B2
(45) Date of Patent: May 22, 2012

(54) APPARATUS FOR SLEEP DISORDER

(76) Inventor: John Edwin McCloud, Wickliffe, OH (US)

(*) Notice: Subject to any disclaimer, the term of this patent is extended or adjusted under 35 U.S.C. 154(b) by 143 days.

(21) Appl. No.: 12/508,685

(22) Filed: Jul. 24, 2009

(65) Prior Publication Data

US 2010/0019107 A1 Jan. 28, 2010

Related U.S. Application Data

(60) Provisional application No. 61/083,685, filed on Jul. 25, 2008.

(51) Int. Cl.
*A47G 29/00* (2006.01)

(52) U.S. Cl. ....... 248/81; 248/160; 248/125.8; 248/166; 5/646

(58) Field of Classification Search ............... 248/161, 248/125.8, 125.2, 124.1, 136, 150, 163.2, 248/157, 165, 166, 436, 176.1, 160, 163.1, 248/170, 168, 188.6, 83, 81, 75, 80; 5/646, 5/638

See application file for complete search history.

(56) References Cited

U.S. PATENT DOCUMENTS

| | | | | |
|---|---|---|---|---|
| 2,748,236 A * | 5/1956 | Landis et al. | ............ | 219/137.51 |
| 2,830,581 A * | 4/1958 | Sanders | ............ | 602/32 |
| 2,911,982 A * | 11/1959 | Guden | ............ | 131/175 |
| 2,963,247 A * | 12/1960 | Collier et al. | ............ | 248/81 |
| 4,541,596 A * | 9/1985 | Price | ............ | 248/125.8 |
| 4,593,688 A * | 6/1986 | Payton | ............ | 128/200.28 |
| 4,744,536 A * | 5/1988 | Bancalari | ............ | 248/125.8 |
| 5,279,486 A * | 1/1994 | Harmon | ............ | 248/122.1 |
| 5,676,158 A * | 10/1997 | Katzman et al. | ............ | 128/845 |
| 5,890,687 A * | 4/1999 | Pryor et al. | ............ | 248/158 |
| 6,695,268 B1 * | 2/2004 | Hsieh | ............ | 248/188.7 |
| 6,916,302 B2 * | 7/2005 | Gehrke | ............ | 602/36 |
| 2007/0045481 A1 * | 3/2007 | Adams | ............ | 248/59 |

FOREIGN PATENT DOCUMENTS

| | | | |
|---|---|---|---|
| GB | 2275605 A * | 9/1994 | |
| WO | WO 2007021969 A2 * | 2/2007 | |
| WO | 2008/021201 | 2/2008 | |

* cited by examiner

*Primary Examiner* — Kimberly Wood
(74) *Attorney, Agent, or Firm* — Rankin, Hill & Clark LLP

(57) ABSTRACT

A device for supporting a flexible hose extending between an individual and a stationary base unit nearby, is disclosed. The support device flexibly supports the hose generally above the individual yet readily accommodates movement by the individual while maintaining communication between the individual and the base unit through the hose. The device is particularly adapted for use by individuals suffering from sleep apnea and who use units to assist in breathing while sleeping or resting. The device can be easily placed into one or more configurations so that it is hidden from view or transportable.

18 Claims, 13 Drawing Sheets

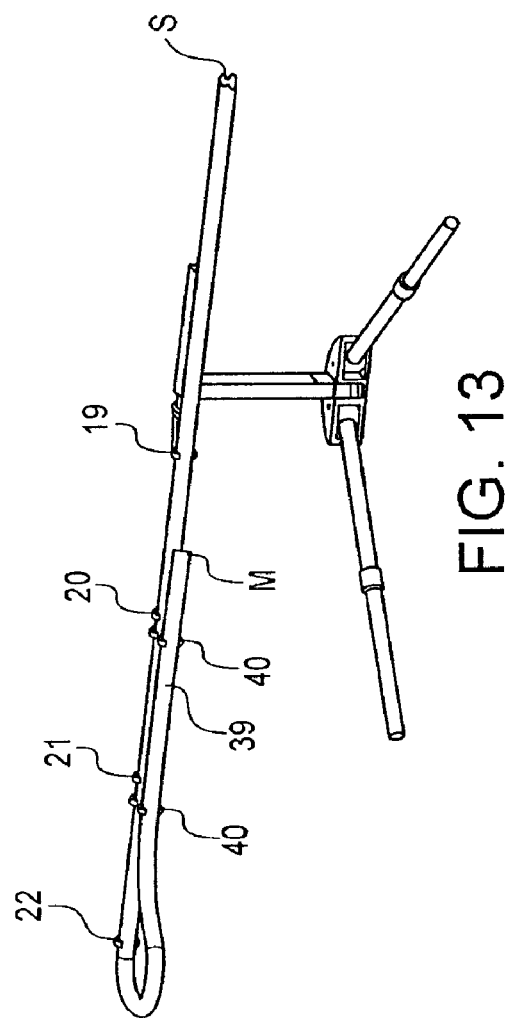
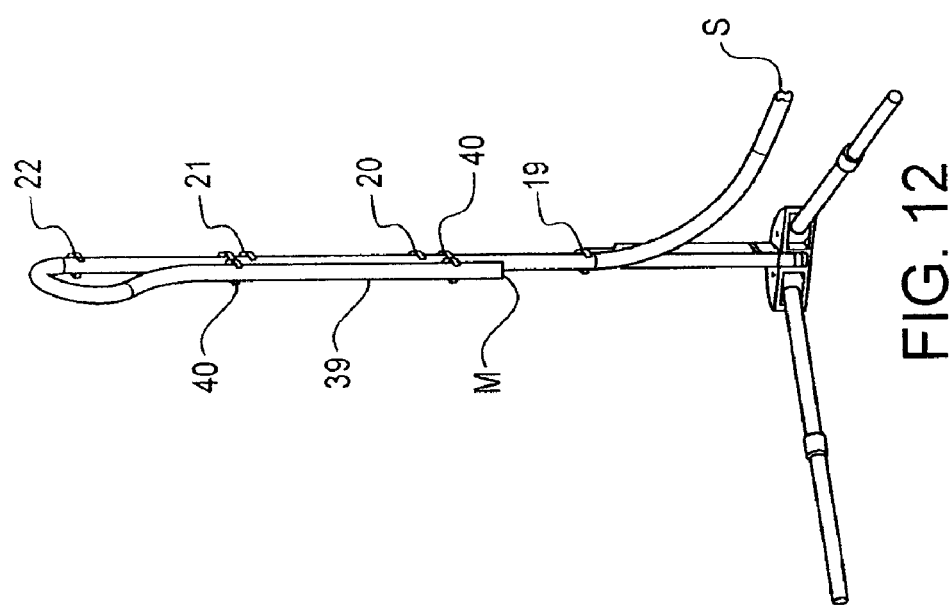

APPARATUS FOR SLEEP DISORDER

CROSS REFERENCES TO RELATED APPLICATIONS

This application claims priority from U.S. provisional application Ser. No. 61/083,685 filed Jul. 25, 2008, which is hereby incorporated by reference.

FIELD OF THE INVENTION

The presently disclosed embodiments are directed to the field of sleep disorders such as for example, sleep apnea.

BACKGROUND OF THE INVENTION

CPAP ("Continuous Positive Airway Pressure") and BIPAP ("Bilevel Positive Airway Pressure") machines are used in treatment for apnea. The treatment typically requires a machine located near a user's bed which supplies air under positive pressure via a hose to a mask worn by the user to keep the user's airway open during sleep. The treatment is effective. However, the user's sleep may be disrupted by the hose as the user moves about during sleep making it difficult to achieve restful sleep.

Various devices are known for supporting a hose over a person's head during rest or sleep, such as described in WO 2008/021201. However, such devices are relatively bulky and cumbersome to move. As a result, after initial assembly alongside a user's bed, these devices typically remain in their initial position and so occupy significant space around the bed and are usually in full view at all times. Furthermore, individuals requiring breathing plenums or hoses, are burdened when traveling with having to disassemble and reassemble such hose supporting devices. This is particularly undesirable when traveling or vacationing at more than one destination. In view of these and other reasons, it would be beneficial to provide a device for supporting a breathing hose above a user's head, such as during sleep or rest, and which did not suffer from the many problems of currently known devices.

SUMMARY OF THE INVENTION

The difficulties and drawbacks associated with previously known devices are remedied by the various preferred embodiment devices that support a flexible hose or tubing that delivers air to a mask worn by an individual while resting or sleeping. The various preferred embodiment support devices eliminate or at least significantly reduce interference of the hose with the wearer, thereby increasing the wearer's comfort and promoting sleep.

The present invention provides a collapsible and portable device for supporting a hose associated with a CPAP or BIPAP machine. The device comprises a base unit having at least two outwardly extending legs. The device also comprises a hose support assembly engaged to and supported on the base unit. The hose support assembly includes a support arm pivotably secured to a support frame. And, the device additionally comprises a telescoping assembly of flexible upper vertical members engaged to and supported on the support arm of the hose support. Each of the upper vertical members includes at least one hose clip member for releasably attaching a hose to be supported.

As will be appreciated, the present invention is capable of other and different embodiments and its several details are capable of modifications in various respects, all without departing from the invention. Accordingly, the drawings and description are to be regarded as illustrative and not restrictive.

BRIEF DESCRIPTION OF THE DRAWINGS

FIG. 12 is another view of the preferred embodiment support device and flexible hose shown in a stowed position.

FIG. 13 illustrates the device of FIG. 12 in a folded state.

DETAILED DESCRIPTION OF THE EMBODIMENTS

Figure 2:
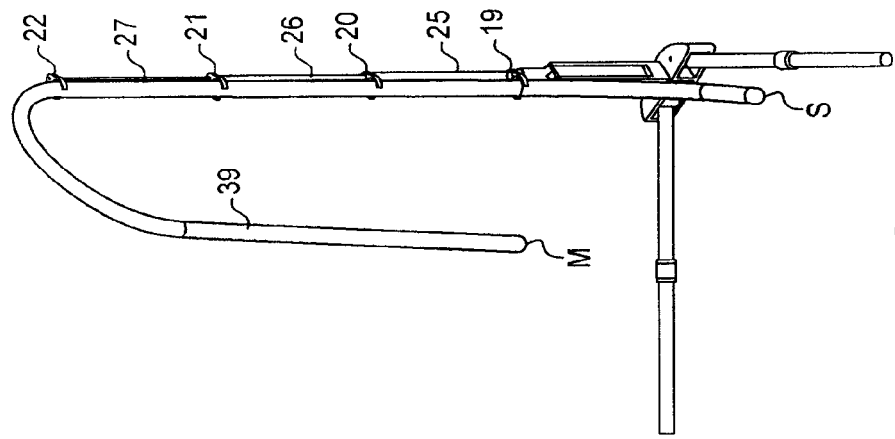
FIG. 2 illustrates the device shown in FIG. 1 supporting a flexible tube in an in-use position with no demand or need for more hose.

The present invention provides various devices and related methods for increasing the comfort of users of CPAP and BIPAP machines. However, the invention and its various embodiments may be used with any treatment that requires a hose or tubing that delivers a gas or fluid to a person.

Specifically, the present invention provides various devices and related methods to readily support a hose or tubing such as used in the treatment of apnea for example, away from the user yet which allows the hose to move freely as the user moves about during sleep. This feature is provided by utilizing a flexible member or a plurality of flexible members to support the hose above the user, and typically, above the user's bed. The flexible members support the hose out of the user's way yet flex when additional hose is required.

The present invention also provides for one or more upper hose support members and hose to be positioned out of sight, such as for daytime storage. This feature is accomplished by utilizing an assembly enabling a hose support assembly to fold or otherwise move one or more upper hose supports from a vertical position to a horizontal position allowing the assembly or at least a portion of the assembly to be hidden out of sight.

Additionally, the present invention is uniquely portable. The invention can be readily collapsed for easy transport or travel without dismantling.

The present invention employs various assemblies that permit one or more of the flexible members to telescope or retract within one another to further promote the portability and ease in storage of the devices. Furthermore, provisions are used that enable one or multiple legs of the devices to be pivoted relative to their base and/or to one another, and in certain embodiments, to retract thereby further promoting the portability and storage aspects of the devices.

References to "vertical" and "horizontal" are frequently used herein to refer to various components and their relative positions. These terms are used with reference to the preferred embodiment support device being positioned alongside a bed when the device is ready for use and in an upright and extended state.

The preferred embodiment devices of the invention include a base assembly generally comprised of one or a plurality of horizontal members or legs secured to the base unit and spaced a sufficient distance apart to enable the one or more legs to be placed between the box spring and mattress of a bed, which is one of several preferred mounting arrangements for the devices. Secured to the base unit, the hose support assembly generally includes a plurality of vertical members generally extending upward, and upon typical positioning of the device, above the mattress of a bed. Preferably, from the base assembly, the plurality of vertical members extend above the mattress to a height great enough to comfortably support the hose away from the user yet provide ample hose to the user.

More particularly, the preferred embodiment devices comprise a base unit which movably engages two or more legs extending outward from the base unit. Each leg preferably includes one or more retractable or telescoping leg sections which can be independently locked into position. Each leg is also preferably positionable and most preferably, pivotally positionable with respect to the base and/or other legs.

The base unit is engaged to a support frame of a hose support assembly. The support frame is preferably movably attached to the base unit and most preferably, hingedly attached to the base unit so that the support frame can be selectively positioned between an upright position in which the frame is transverse to the plane in which the legs extend, and a lowered position in which the frame is generally disposed in the same plane as the legs. Preferably, the hose support assembly is selectively positionable with respect to the base unit, and positionable between (i) an extended vertical position and (ii) a retracted position in which the hose support assembly is coplanar with the legs.

The support frame supports, retains, and preferably movably retains a support arm of the hose support assembly. The support arm is sized and shaped to engage a receiving channel or open region defined along a majority of the length of the support frame. As described herein, the support arm is preferably hinged or pivotally attached to the support frame so that the arm can be selectively positioned between an upright position in which the arm is transverse to the plane in which the legs extend, and a lowered position in which the arm is generally disposed in a plane parallel to the plane of the legs. Specifically, the support arm of the hose support assembly is selectively positionable with respect to the support frame of the hose support assembly and positionable between (i) an extended vertical position and (ii) a horizontal position.

A slidable release member can be used to lock the support arm in an upright position. Preferably, the plane in which the support frame can be pivoted relative to the base unit is different than, and most preferably perpendicular to, the plane in which the support arm can be pivoted relative to the support frame. Restated, the plane in which the support arm can be pivoted relative to the base unit is different than, and most preferably perpendicular to, the plane in which the support frame can be pivoted relative to the base unit.

Secured to the support arm, is one or more hose support members. Preferably, the present invention utilizes two or more, such as three support members. Additional numbers of such members are also contemplated. As described herein, preferably the hose support members are sized and configured such that they telescope into an adjacent larger sized member, thereby providing a collapsible telescoping assembly of support members. These members are preferably flexible to allow movement of the hose as described herein.

The present invention hose support devices preferably also utilize one or more clips or other engagement members to releasably secure the hose to regions of the device and/or to the hose itself.

Generally, the term "base assembly" as used herein refers to members 10, 11, 12 and 41. The term "hose support assembly" refers to members 15, 16, 18, 25-27 and 38. Also, pivot points and holes are shown without screws, pins or bolts to promote clarity.

Figure 1:
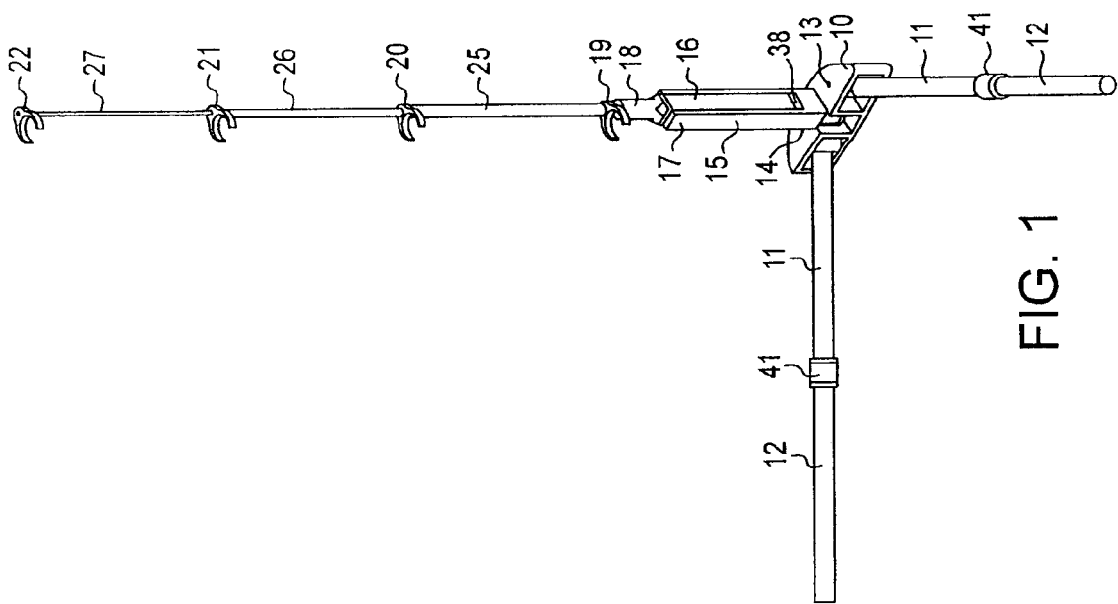
FIG. 1 illustrates a preferred embodiment support device shown without a flexible tube or hose, the device being in an extended and at-rest position.

FIG. 1 shows a preferred embodiment support device with a base assembly comprising a base unit 10 with two outwardly extending horizontal major legs 11 and corresponding telescoping minor leg members 12, extended sufficient to provide stability between a mattress and box spring, when the legs 11 and members 12 are inserted therebetween. Preferably, the major legs 11 define a generally hollow interior sized and configured to slidably receive the minor legs 12. Preferably, each leg or leg assembly is pivotable with respect to the base unit. Telescoping members 12 are shown locked into position by extension locking members 41. Additionally, shown is a hose support assembly comprising a support frame 15 and a support arm 16 which is hingedly secured to the support frame 15 about a pivot 17. Preferably, the hose support is positionable between an extended vertical position and a retracted horizontal position. The support arm 16 includes a relatively rigid vertically extending portion 18 (via member 38) that as explained in greater detail herein, engages and retains a lowermost upper vertical support member. The support arm 16 also includes a slidable release member 38 which governs whether the arm 16 is free to pivot relative to the support frame 15. Also illustrated are telescoping flexible upper vertical members 25-27 onto which a hose can be readily attached using hose clip members 19-22.

Figure 4:
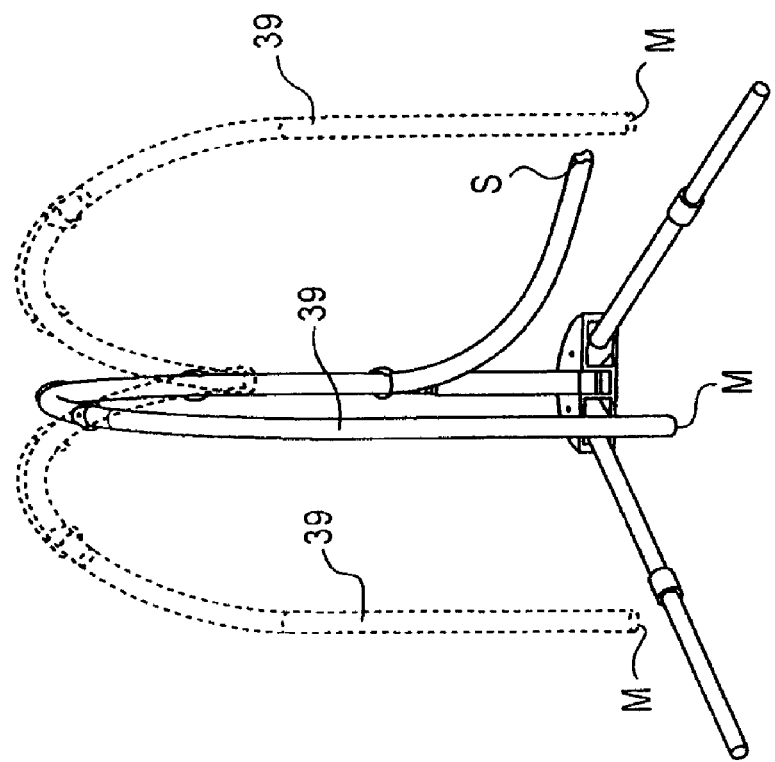
FIG. 4 illustrates the support device of FIG. 3 supporting the flexible tube and further illustrates various laterally extended positions for the supported flexible tube in phantom lines.
Figure 3:
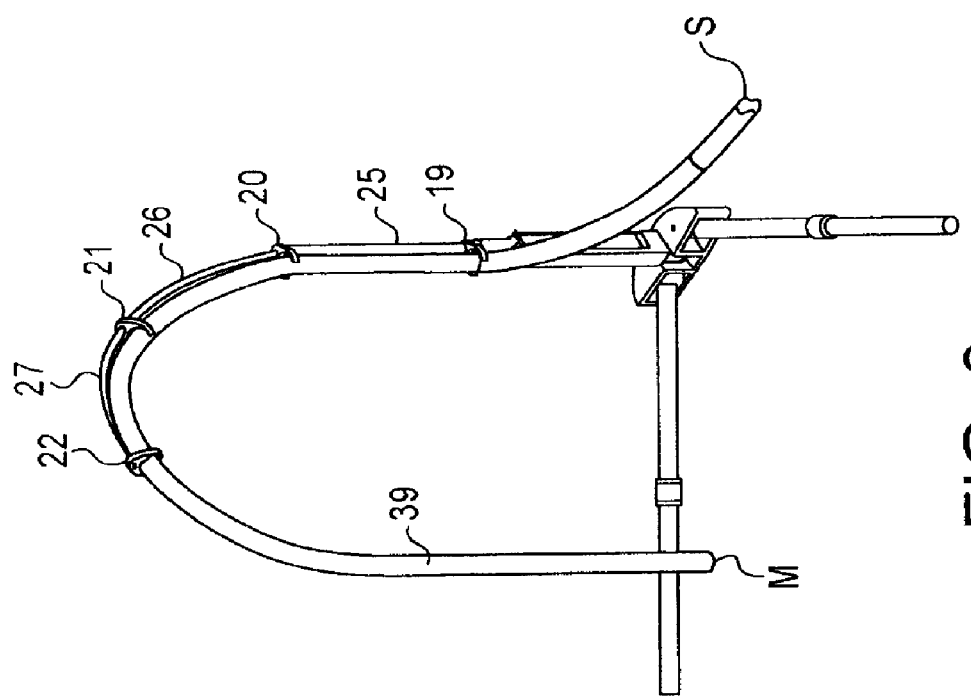
FIG. 3 illustrates the support device of FIG. 2 supporting the flexible tube in an in-use position with a demand or need for hose.

FIGS. 2-4 illustrate the preferred embodiment support device supporting a flexible hose 39. These figures illustrate the ability of the flexible members 25-27 to keep the hose suspended away from the user yet flex in any lateral direction to thereby provide extra hose when necessary, thus providing maximum comfort for the user. Typically, one end S of the hose 39 is connected to a source of pressurized air, such as provided by a CPAP or BIPAP machine. The other end of the hose designated as M is attached to a mask which is worn by a user, typically during rest or sleep. Specifically, FIG. 2 illustrates the preferred embodiment device with the upper vertical members 25-27, and hose clips 19-22 in an upright position supporting the hose 39 without any downward load, force, or demand for additional hose. FIG. 3 illustrates how the device's upper vertical members 25-27 flex thereby providing additional hose 39 to the user as needed. FIG. 4 illustrates how the upper vertical members 25-27 flex to either side to respond to movements by an individual such as during sleep.

Figure 5:
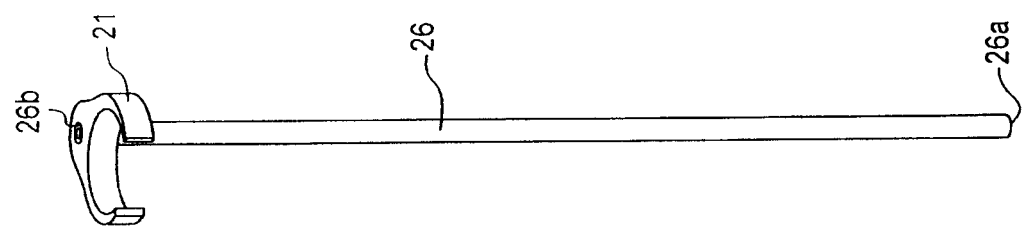
FIG. 5 illustrates a vertical support member used in the preferred embodiment device of FIG. 1.

FIG. 5 is a view of a single telescoping upper vertical flexible member 26 and hose clip member 21 used to attach the hose 39 to the flexible member 26. It will be understood that the flexible member 26 and its corresponding clip member 21 are representative of the other upper vertical flexible members 25 and 27 and their clip members 19 (19 is attached to member 38), 20, and 22. One or more hose clip members can be used in conjunction with each flexible member. Furthermore, the one or more hose clip member(s) can be located anywhere along the length of the flexible member. However, when utilizing a telescoping assembly of flexible members as described herein, it is preferred that the clip member, such as clip member 21 be positioned at an end of the flexible member such as end 26b shown in FIG. 5. It will be understood that this configuration enables the other end 26a of the flexible member 26 to be inserted into a hollow interior of its adjacent flexible member having a larger diameter, of the telescoping assembly of flexible members 25-27.

Figure 6A:
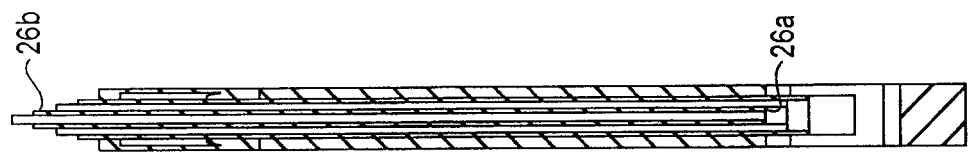
FIG. 6A is a cross sectional view taken along line AA in FIG. 6 illustrating the collapsed assembly.
Figure 6:
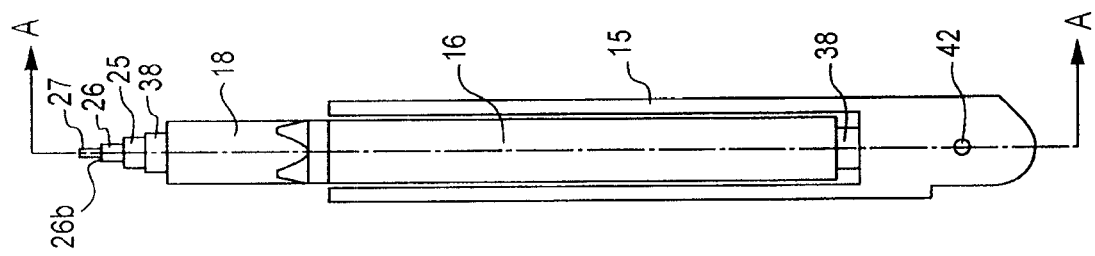
FIG. 6 is a partial sectional view illustrating a collapsed assembly of vertical support members used in the preferred embodiment device of FIG. 1.

FIG. 6 is a partial sectional view illustrating a collapsed or retracted assembly of telescoping flexible members 25-27, the support arm 16, and the support frame 15. Preferably, each member 25-27 is hollow and slightly smaller in diameter than a neighboring member, thereby providing the ability for the members to slide or telescope into one another. That is, in the preferred telescoping assembly, the span of the interior hollow region of a member is slightly larger than the outer span of an adjacent member. Thus, an upper vertical member, i.e. 25-27, is preferably slidably received in an adjacent and larger vertical member. Portion 18, as previously noted, serves to support a lowermost vertical support member such as member 25. It will be appreciated that the vertical members having a larger span or diameter will be located closer to the support arm 16 than the members having smaller spans. Although the invention includes a wide range of configurations for the upper vertical members 25-27, preferably, each member is in the form of a hollow cylinder, and the assembly of members 25-27 are concentrically arranged along a common center axis. For clarity, the hose clip members 19-22 are not shown in FIG. 6. FIG. 6A is a cross sectional view taken along line AA of FIG. 6 further illustrating the relationship between the members 25-27 when in a collapsed state. The ends 26a and 26b of the member 26 are shown in FIG. 6A.

Although a telescoping configuration for the upper vertical members is depicted, such as in FIG. 6A, it will be appreciated that the present invention includes other assemblies and arrangements. Such as, instead of utilizing a telescoping assembly in which each member is slidably received into an adjacent member along their longitudinal axes, it is contemplated that a hinged configuration could be used. In this hinged configuration, each member would be hingedly attached to its adjacent neighboring members. Upon extending or unfolding the collection of members, locking devices could be used to secure each member in a desired extended position.

Figure 9:
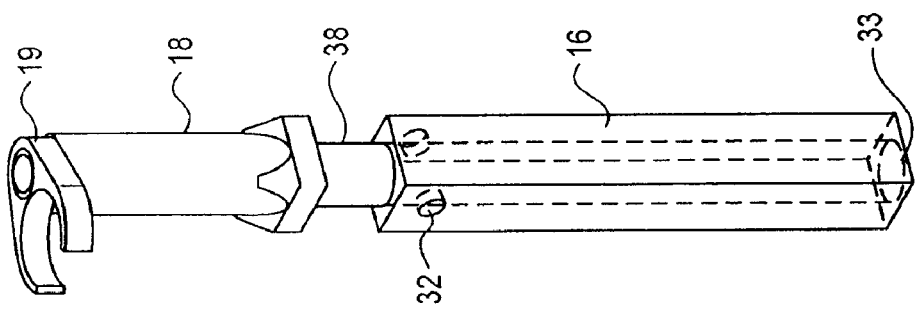
FIG. 9 is a perspective schematic view of the support arm of FIG. 8, shown in a disengaged position when retained in the frame.
Figure 8:
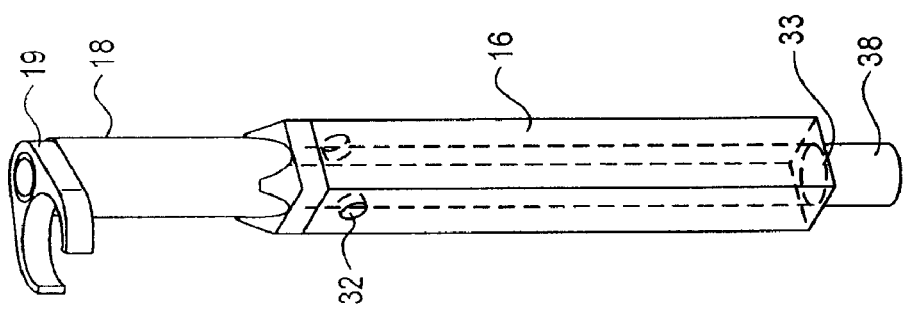
FIG. 8 is a perspective schematic view of a support arm retained in the support frame depicted in FIG. 7, the support arm shown in an engaged position when retained in the frame.
Figure 7:
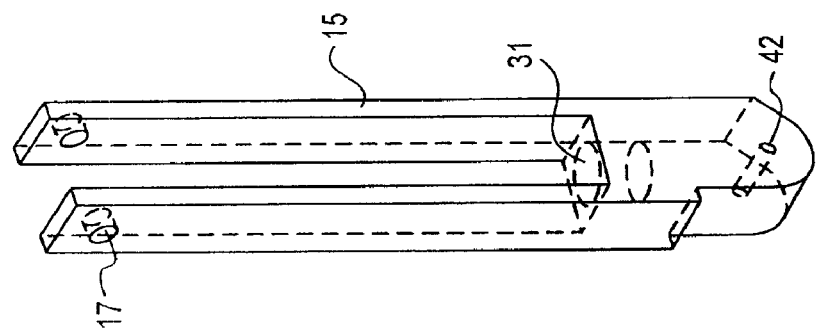
FIG. 7 is a perspective schematic view of a support frame used in the preferred embodiment device of FIG. 1.

FIGS. 7-9 illustrate the support frame 15 and the support arm 16, showing how a slidable release member 38 provides a means to lock the support arm 16 into a vertical position or rather in a position parallel to the longitudinal axis of the support frame 15. A preferred configuration for such locking assembly is to provide the support arm 16 with an interior channel 33 extending along at least a portion of the length of the arm 16 in which the release member 38 is slidably disposed. A corresponding receiving channel 31 is defined along an upward facing surface of the support frame 15 and aligned with the release member 38 when the support arm 16 is disposed within or alongside and parallel with the support frame 15. Thus, it will be understood that when the support arm 16 is oriented parallel with the support frame 15, the release member 38 can be slidably extended from its channel 33 in the arm 16, and urged into the receiving channel 31 of the support frame 15. FIG. 8 illustrates the support arm 16 and member 38 in a locked position, evidenced by the lower portion of member 38 protruding from a lower portion or end of the arm 16 a sufficient distance to engage the support frame 15 by insertion into the channel 31 defined therein. FIG. 9 shows member 38 in an unlocked position in which the member 38 does not protrude from the lower region of the support arm 16 and thereby does not enter the channel 31 of the support frame 15. The upper end of the slidable member 38 contacts, is secured to, or may be integral with, the portion 18.

Also shown in FIGS. 7-9 are various apertures or holes that are used in a pivot assembly which enables the support arm 16 to be pivoted or otherwise selectively positioned relative to the support frame 15. Preferably, holes 17 are defined in the upper region of the support frame 15 and a corresponding hole 32 is defined in the support arm 16. The holes 17 and 32 are sized and aligned such that when the arm 16 is disposed in or alongside the support frame 15, one or more pivot pins or axles (not shown) can be inserted through the holes 17 and 32. Preferably, the pivot pins do not actually go all the way through the support arm 16. The pivot pins preferably only enter from each side enough to retain the support arm yet not interfere with member 38's ability to slide within the support arm. The present invention includes a wide range of assemblies for hinging support arm 16 to the support frame 15.

Figure 10:
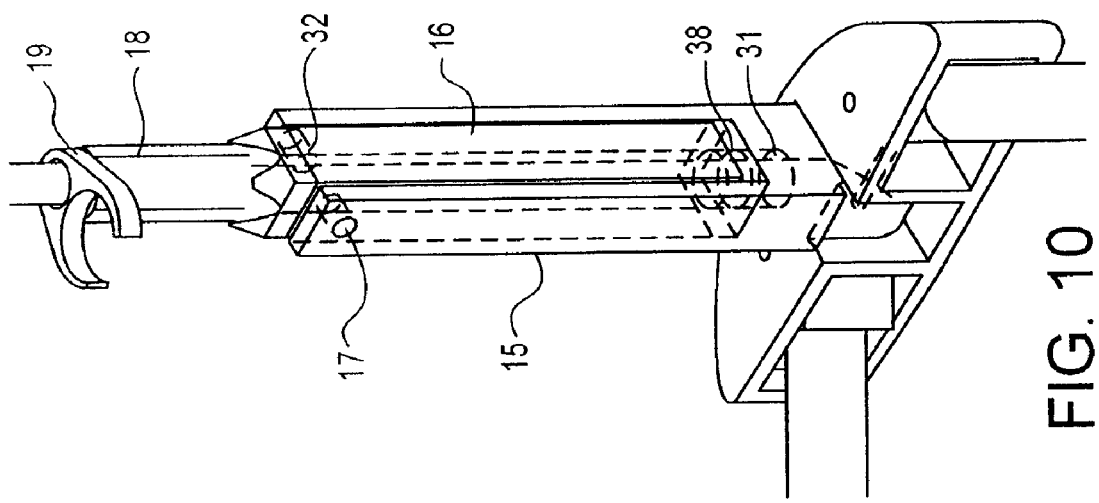
FIG. 10 is a detailed schematic view of the support arm hingedly affixed and retained in the support frame, the frame affixed to or otherwise integral with a base member used in the preferred embodiment support device such as shown in FIG. 1.

FIG. 10 illustrates the preferred embodiment support device with the support arm 16 disposed within the support frame 15. The support arm 16 is vertically oriented and parallel with the support frame 15. It will be appreciated that in this position, the slidable release member 38 can be extended from the lower portion of the support arm 16 and inserted into the channel 31 defined in the support frame 15 to lock the arm 16 in the noted position relative to the frame 15. FIG. 10 also illustrates a pivot engagement between the support arm 16 and the support frame 15 provided by a pivot pin (not shown) extending through corresponding sized and aligned apertures 17 and 32 defined in the support frame 15 and the support arm 16.

Figure 11:
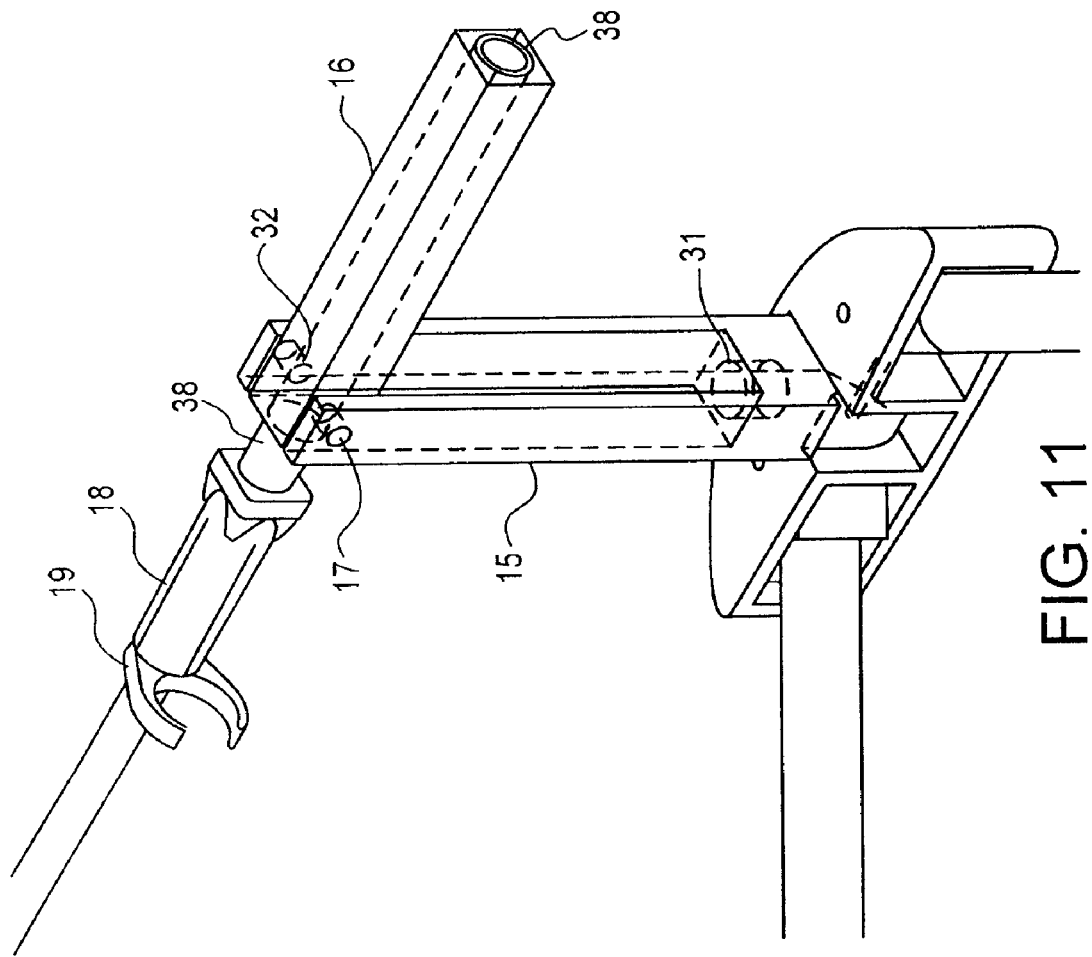
FIG. 11 illustrates the assembly of FIG. 10 in which the support arm, in a disengaged position, is hingedly pivoted to the support frame.

FIG. 11 illustrates the support device with the arm 16 rotated into a horizontal position after placing member 38 in an unlocked position in which the member 38 does not protrude from the lower region of the arm 16 and thereby does not enter the channel 31 of the support frame 15. Specifically, FIG. 11 illustrates the ability for the upper flexible members 25-27 and hose clips 19-22 to be stored horizontally and out of view when not in use by moving or rotating the support arm 16 from a vertical position to a horizontal position. As noted, the support frame 15 provides a pivot about which the support arm 16 is rotatably attached, thereby enabling the support arm 16 to rotate, pivot, or otherwise move between vertical and horizontal positions relative to the vertically extending support frame 15.

FIG. 12 illustrates the preferred embodiment support device in a vertical position ready to pivot or otherwise move into a horizontal position. The loose section of hose 39 adjacent the end M, is kept secure by using double hose clips 40. That is, one or more double hose clips or other engagement members described in greater detail herein, are preferably used to retain a selected region of the hose to another region of the hose.

FIG. 13 illustrates the preferred embodiment support device and hose in a folded position. As will be understood, the support arm 16 is unlocked from the support frame 15 and pivoted about the noted pivot using holes 17 and 32 as previously described, to the position shown. This folded position may be desirable for placing the device and a hose 39 attached thereto in a position generally hidden from view, as the device is typically positioned and held alongside a bed by inserting the legs 11 and 12 between a mattress and box spring. FIG. 13 depicts the upper vertical flexible members 25-27, hose clips 19-22 and hose 39 rotated or moved to a horizontal position as may be desired for daytime storage with the double hose clip members 40 keeping the free section of hose in place.

Figure 14:
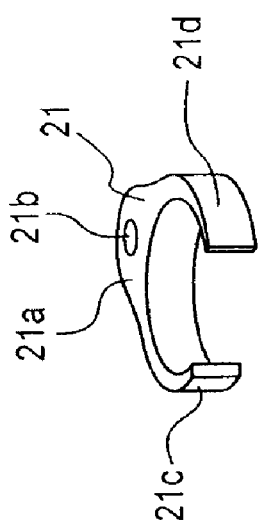
FIG. 14 is a perspective view of a preferred hose retention member used in the preferred embodiment support device of FIG. 1.

FIG. 14 illustrates in greater detail a preferred hose clip member 21, and is representative of any of the hose clip members 19-22. The hose clip member preferably includes a body portion 21a defining an aperture 21b sized to receive and fittingly engage a respective vertical member such as one of members 25-27. The hose clip also preferably includes two outwardly extending flexible prongs 21c and 21d that releasably attach and engage the hose 39 along its outer periphery. It will be appreciated that the hose clip members, e.g. members 19-22, may be integrally formed with corresponding upper vertical flexible members, i.e. members 25-27. Thus, referring to FIG. 5 for example, the hose clip member 21 could be integral with the member 26.

Figure 15:
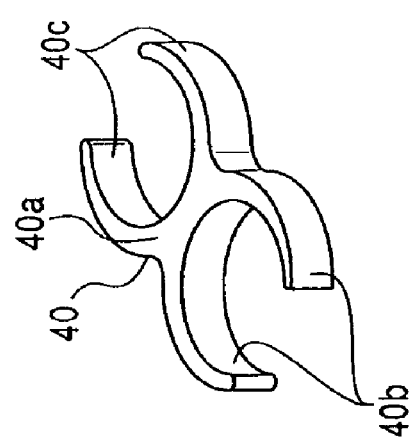
FIG. 15 is a perspective view of a preferred hose stowage member used in the preferred support device of FIG. 1.

FIG. 15 illustrates in greater detail a preferred double hose clip member 40. The double clip 40 is used to connect the otherwise loose section of hose to the section of hose held in place by hose clip members 19-22, thus keeping the hose in place parallel to the flexible members 25-27 which is particularly desirable when the support arm 16 is rotated into a horizontal position as shown in FIG. 13. As depicted in FIG. 15, the preferred double hose clip member 40 includes a body portion 40a and two pairs 40b and 40c of oppositely directed prongs that are sized and configured to releasably engage regions of the hose.

Figure 16:
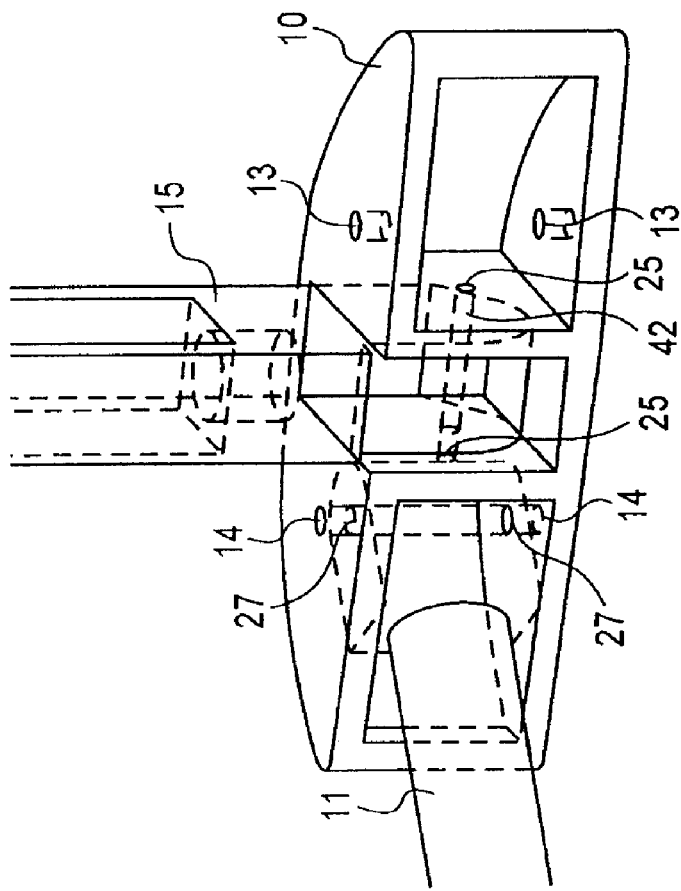
FIG. 16 is a partial schematic detailed view illustrating the base member and its hinged affixment to the support frame, and an outwardly pivoted leg.
Figure 18:
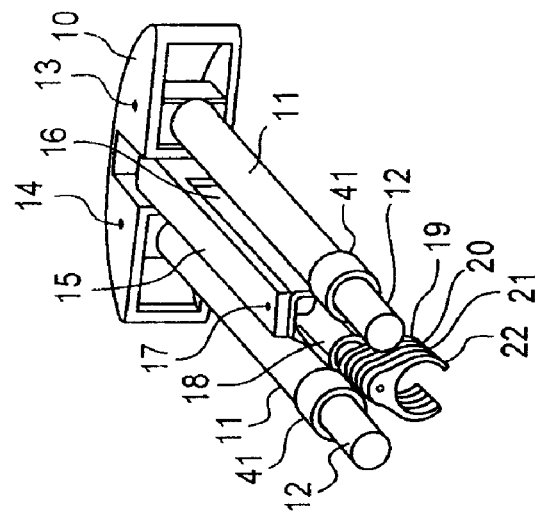
FIG. 18 is a perspective view of the preferred embodiment support device depicted in FIG. 17 in a fully collapsed state.
Figure 17:
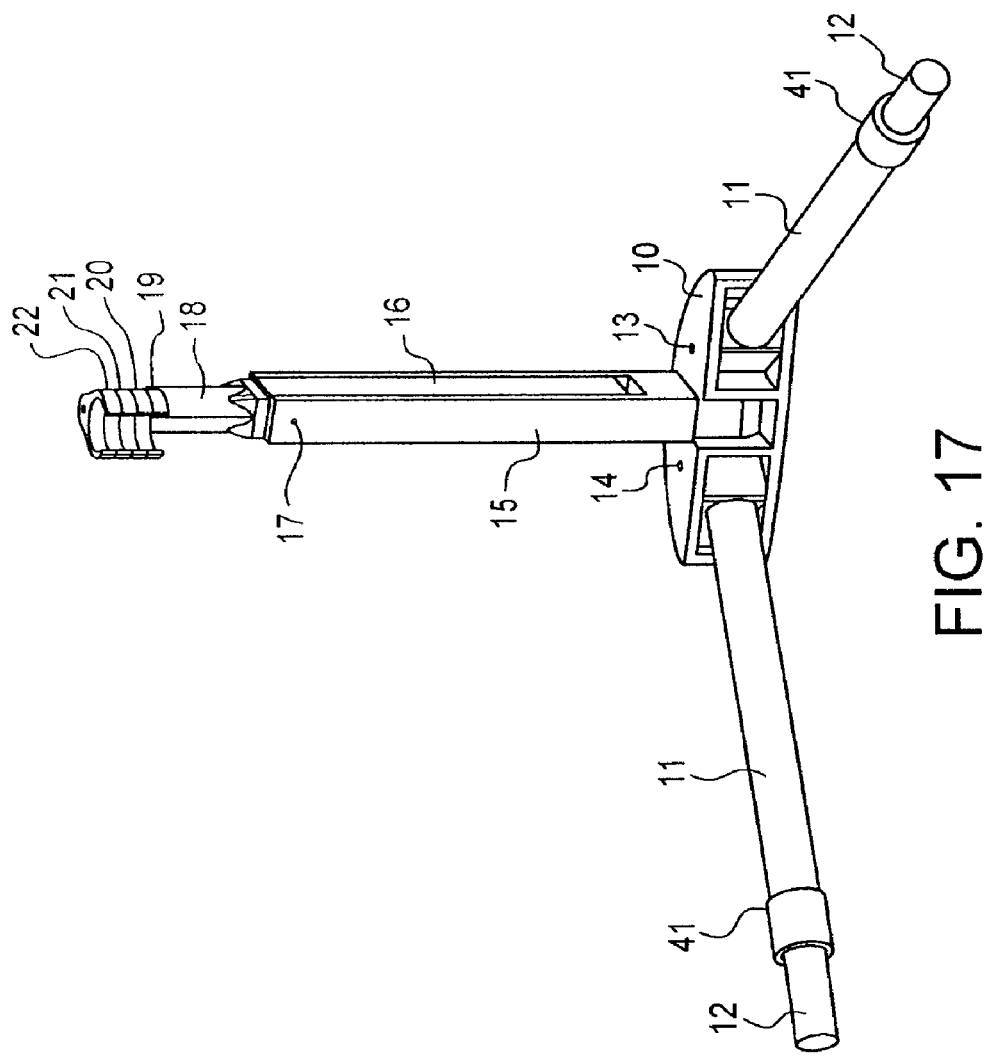
FIG. 17 is a perspective view of the preferred embodiment support device of FIG. 1 in a partially collapsed state illustrating two outwardly pivoted legs, each leg in a retracted position.
Figure 19:
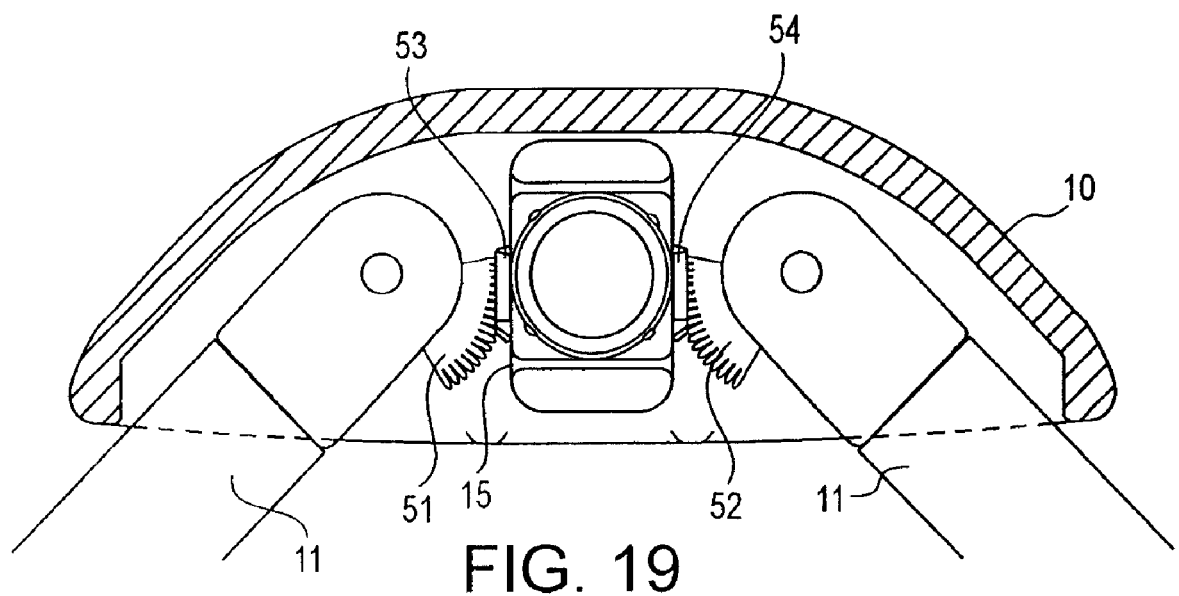
FIG. 19 is a partial cross sectional planar view of the base member and its engagement with two legs, each leg in an outwardly pivoted position.
Figure 20:
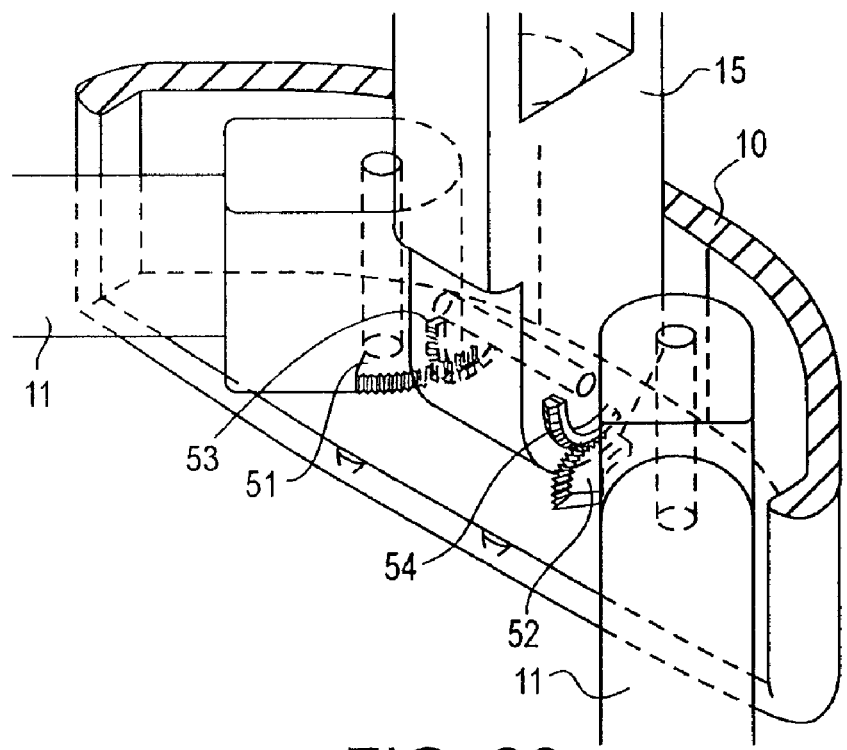
FIG. 20 is a cross sectional schematic perspective view further illustrating the base member and outwardly pivoted legs.
Figure 21:
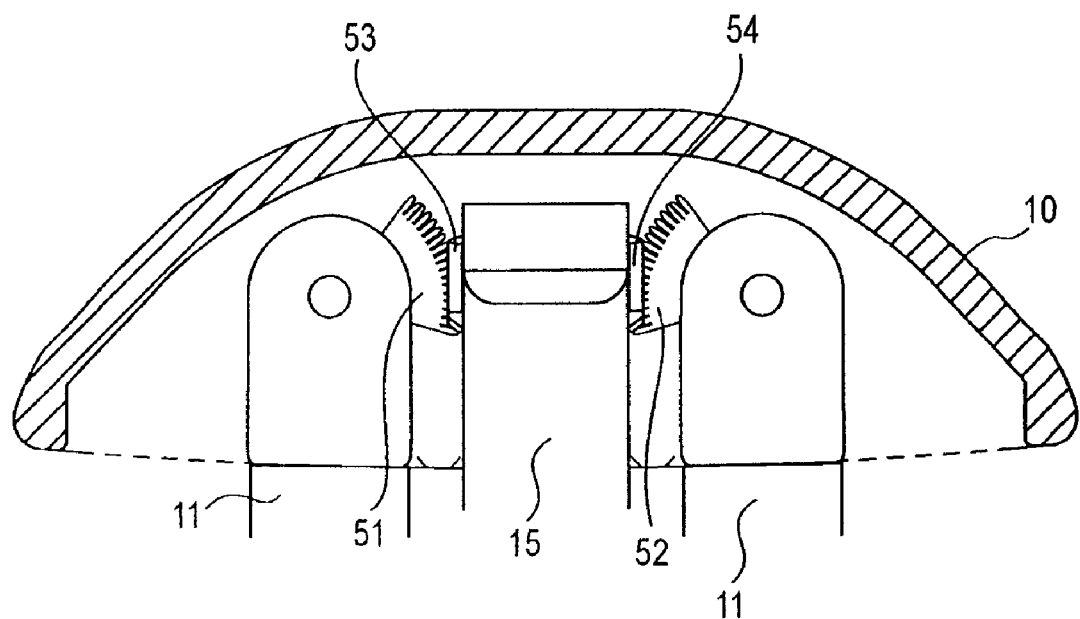
FIG. 21 is a partial cross sectional view of the base member and legs, each leg in an inwardly pivoted position.
Figure 22:
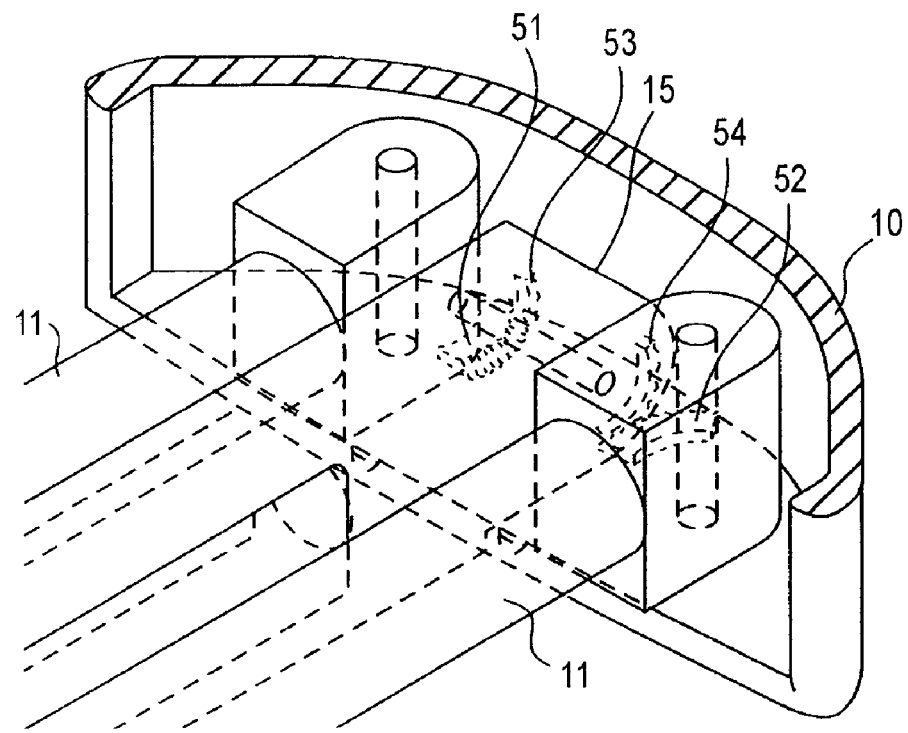
FIG. 22 is a cross sectional schematic perspective view illustrating the base member and inwardly pivoted legs.
Figure 23:
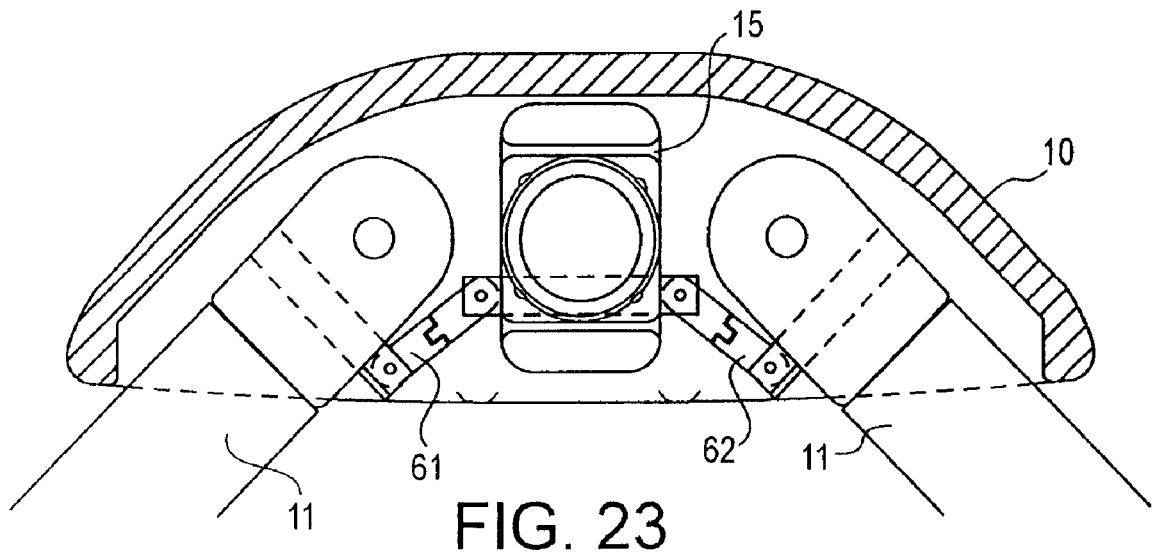
FIG. 23 is a partial cross sectional planar view of another version of the base member and its engagement with two legs, each leg depicted in an outwardly pivoted position.
Figure 24:
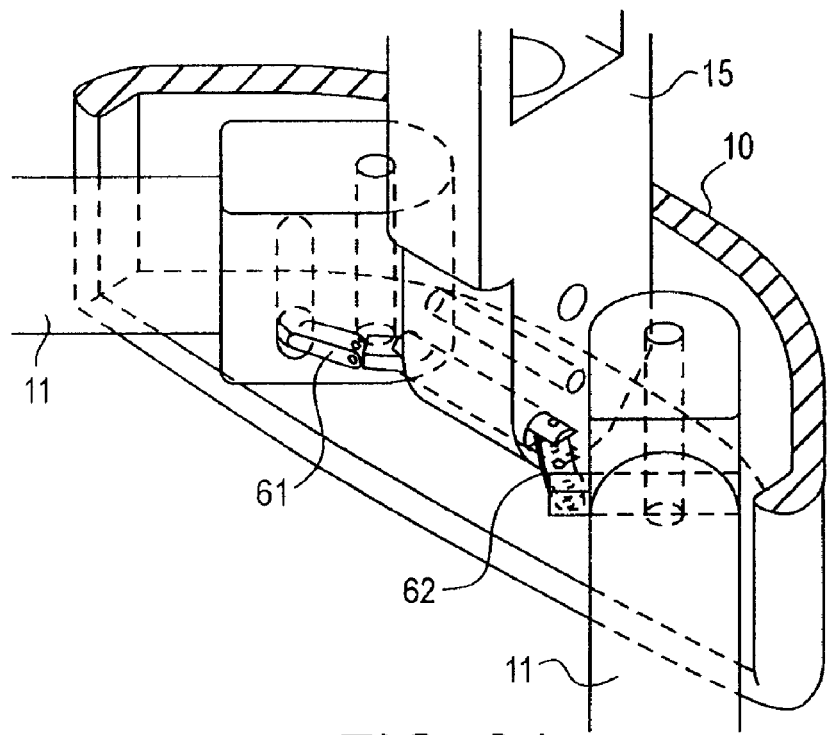
FIG. 24 is a schematic cross sectional perspective view further illustrating the base member and outwardly pivoted legs of FIG. 23.
Figure 25:
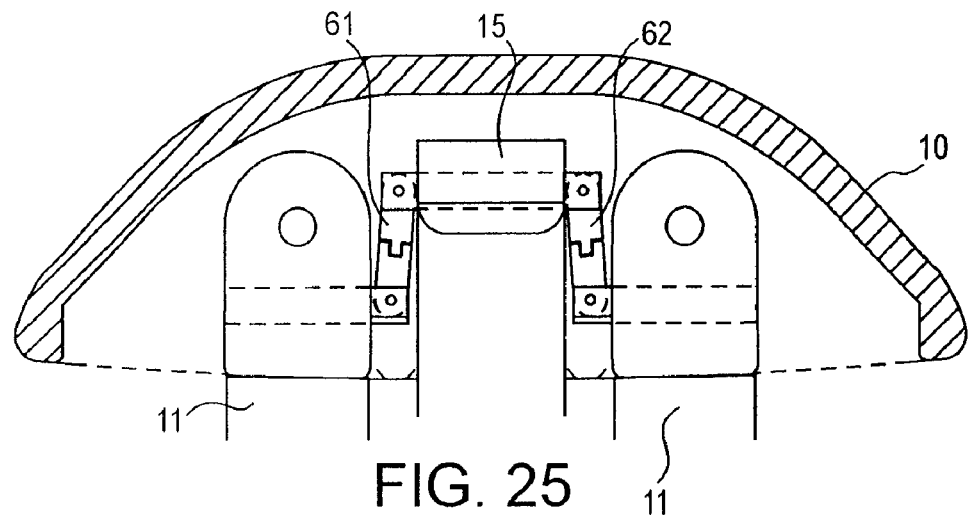
FIG. 25 is a partial cross sectional planar view of the base member and legs of FIG. 23, each leg being in an inwardly pivoted position.
Figure 26:
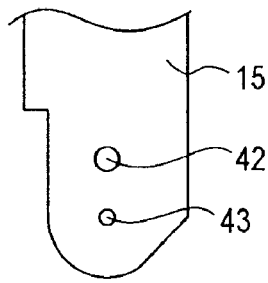
FIG. 26 is a detailed view illustrating a proximal end of a support frame used in the assembly of FIG. 23.
Figure 27:
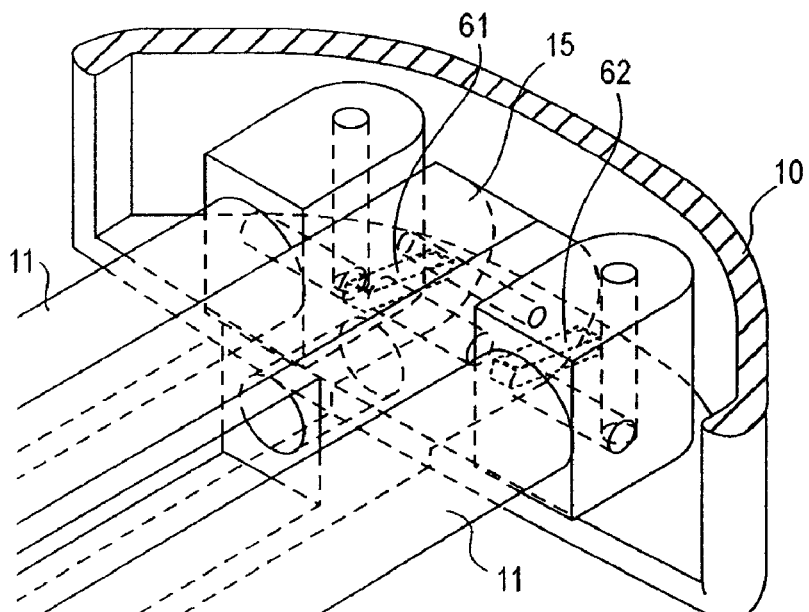
FIG. 27 is a schematic cross sectional perspective view illustrating the base member and inwardly pivoted legs of the assembly of FIG. 23.

FIGS. 16-18 illustrate a feature of the preferred embodiment support device which enables the device to collapse to a relatively small size for storage or travel without dismantling. FIG. 16 shows the base unit 10 defining a horizontally extending hole 25 in two interior walls of the base, the holes 25 serving as a pivot point for the support frame 15 having a corresponding horizontally extending hole 42. It will be appreciated that a pivot pin (not shown) is disposed within the aligned holes 25 and 42. This pivot assembly allows the support frame 15 and its connected members, i.e. the support arm 16 and flexible members 25-27, to move or rotate from a vertical to a horizontal position. FIG. 16 also shows base unit 10 having vertical holes 13 and 14 which are used in pivot assemblies for the legs 11 having vertically aligned holes 27 defined in each of the legs 11. Again, it will be appreciated that vertically oriented pivot pins (not shown) extend through a pair of holes 14 and 27 to provide a pivot assembly for a first leg 11, and through another pair of holes 13 and 27 to provide a pivot assembly for a second leg 11 (not shown in FIG. 16). The pivot assemblies allow the major legs 11 and their extension members, i.e. the minor legs 12 to pivot, i.e. move closer to one another or away from one another, a sufficient degree as to provide a stable base for the assembly. Thus, preferably each of these telescoping leg assemblies is pivotable with respect to the base unit.

FIG. 17 depicts the device with the upper flexible members 25-27 collapsed and generally hidden from view resulting in hose clips 19-22 to stack as shown. Also shown, are legs 11 with leg extension members 12 retracted or collapsed and locked in place using members 41. FIG. 18 depicts the device in its closed or compact state ready for transport or storage. The support frame 15 and its connected members have been pivoted to a horizontal position using the pivot assembly employing holes 25 and 42 as previously described. The legs 11 and telescoping legs 12 have been pivoted toward one another and close to support frame 15 using pivot assemblies employing holes 13,14 and 27 as previously described.

In certain versions of the device, it may be preferred to couple movement or pivoting of the support frame 15 to one or more legs 11. FIGS. 19-22 illustrate by the use of gears, how the legs may be engaged to open and close by the pivotal motion of the support frame 15 moving between its vertical position and its horizontal position. By using a gear ratio of 1 to 0.5 for example, when the support frame 15 moves 90 degrees for example from its vertical position relative to the base 10 to its horizontal position, the legs 11 will also rotate or move 45 degrees for example thereby bringing them into the closed position. Although the present invention includes the use of nearly any gear assembly, gear orientation, and gear ratio, a preferred gear assembly is depicted in FIGS. 19-22. There, a first leg gear 51 affixed to a leg 11 is engaged with a first support frame gear 53. A second leg gear 52 affixed to another leg 11 is engaged with a second support frame gear 54.

FIGS. 23-27 illustrate another preferred assembly for linking the legs 11 so that they open and close according to pivotal movement of the support frame 15. As the support frame 15 rotates about the pivot assembly employing hole 42 defined in the frame 15, linkage to an aperture 43 radially spaced from the hole 42, creates motion that may be utilized by other linkages to move the legs 11, such as for example 45 degrees when the support frame 15 moves 90 degrees from its vertical position to its horizontal position. Other angles and ratios between such angles are encompassed by the present invention. Specifically, a first linkage assembly 61 is provided movably connecting a leg 11 to the support frame 15. A second linkage assembly 62 is provided movably connecting another leg 11 to the support frame 15.

Figure 28:
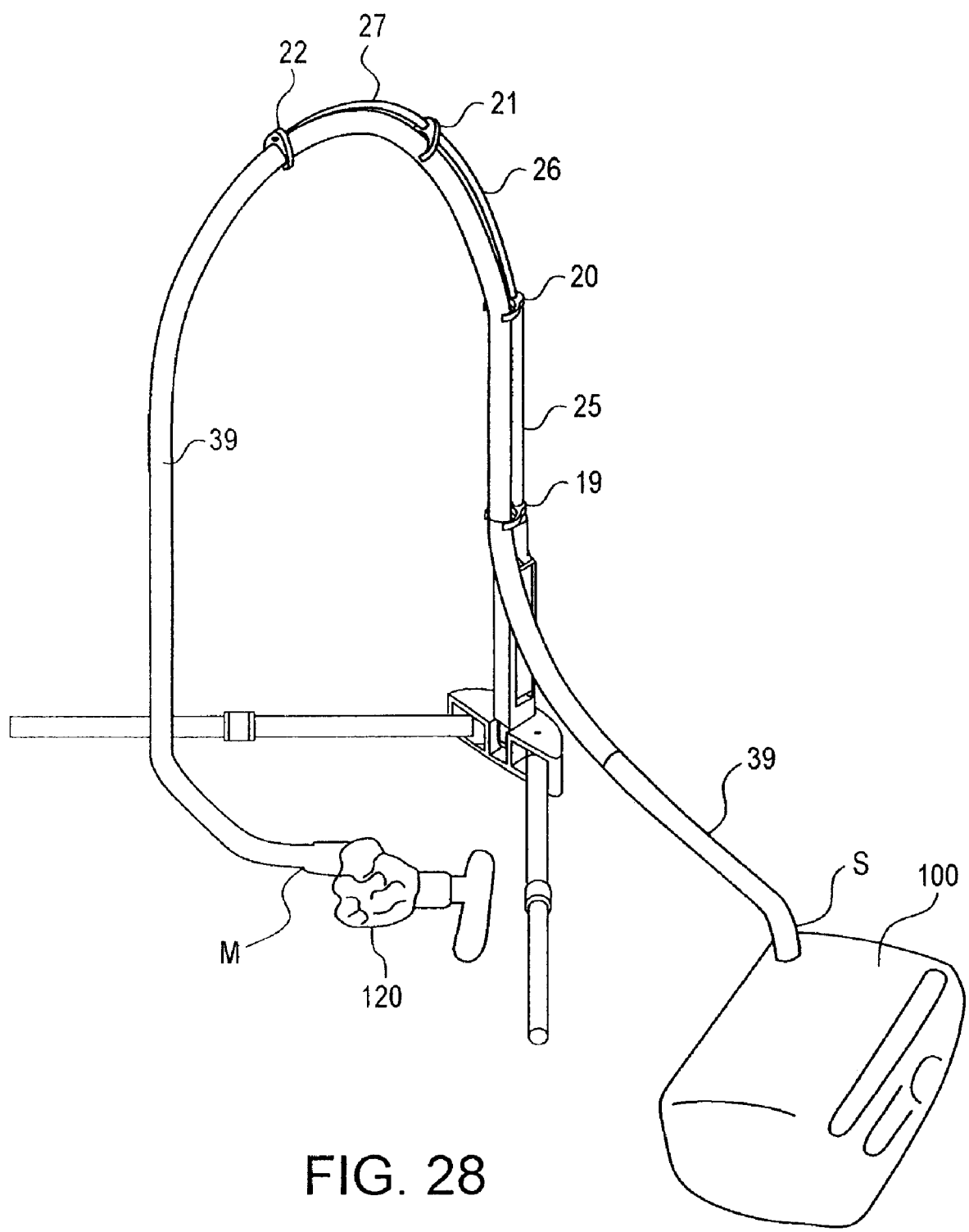
FIG. 28 illustrates a CPAP or BIPAP machine having a hose extending therefrom and the hose being supported by a preferred embodiment device in accordance with the present invention.

FIG. 28 illustrates a CPAP or BIPAP machine having a hose extending therefrom and supported by a preferred embodiment device in accordance with the present invention. Specifically, the preferred embodiment device is depicted in an extended, upright configuration such as ready for use. The device is shown supporting a hose 39. One end of the hose 39 designated as S, is connected to an air outlet of a CPAP or BIPAP machine designated as 100. The other end of the hose 39, designated as M, is connected to a mask 120 which is worn by a user.

CPAP and CIPAP machines are commercially available from numerous sources such as for example, Aeiomed of Minneapolis, Minn.; Cardinal Health of Dublin, Ohio; DeVilbiss HealthCare of Sommerset, Pa.; Fisher & Paykel HealthCare of Irvine, Calif.; Invacare of Elyria, Ohio; Puritan Bennett, a division of Covidien of Boulder, Colo.; ResMed of San Diego, Calif.; and Respironics, a division of Philips of Andover, Mass.

The present invention also includes an embodiment in which the hose support is configured such that the unit is disposed on the floor rather than between a mattress and box spring. In this embodiment, it is preferred to use at least three or more legs, to provide a tripod-like base. Alternately, it is contemplated that other configurations of assemblies instead of legs could be used including for example flat horizontal panels that contact the floor with one or more vertically extending members to support the device.

The present invention also includes an embodiment in which the upper members such as the support frame 15 is mounted to a headboard or wall rather than using the base 10 and legs 11 as illustrated herein. It is also contemplated that the hose support device could be attached or otherwise supported by a CPAP or BIPAP machine, or by a table or enclosure for such machine.

The base unit and, support frame, support arm, and legs may be made of any form or combination of plastic, carbon composite, graphite, fiberglass, metal or other material sufficient to cut, mold or to otherwise manufacture to size and shape necessary to fulfill the members function.

The upper vertical members are preferably formed from a material with sufficient rigidity to support the hose away from the user yet flexible enough to flex providing additional hose when needed as the user moves about during sleep. The upper vertical members may be made of any form or combination of plastic, carbon composite, graphite, fiberglass, metal or other material sufficient to cut, mold or to otherwise manufacture to size and shape necessary to provide sufficient support and flexibility.

The vertical members may have cross sectional shapes that are round, square, triangular, flat or any other shape so long as they provide sufficient rigidity to support the hose away and yet flex sufficiently to provide additional hose to the user as necessary.

It will also be understood that the present invention devices may also be used for supporting wires or cables in addition to or instead of, hoses or tubing as shown herein. Many applications exist in which wires or cables extend between a person and a medical instrument for example. Such wires or cables are ideally suspended above the person yet in such a manner that the person can move about.

Many other benefits will no doubt become apparent from future application and development of this technology.

As described hereinabove, the present invention solves many problems associated with previous type devices. However, it will be appreciated that various changes in the details, materials and arrangements of parts, which have been herein described and illustrated in order to explain the nature of the invention, may be made by those skilled in the art without departing from the principle and scope of the invention.

What is claimed:

1. A collapsible and portable device for supporting a hose associated with a CPAP or BIPAP machine, the device comprising:
   a base unit having at least two outwardly extending legs;
   a hose support assembly engaged to and supported on the base unit, the hose support assembly including a support frame and a support arm pivotably secured to the support frame, wherein the support frame is pivotably secured to the base unit; and
   a telescoping assembly of flexible upper vertical members engaged to and supported on the support arm of the hose support, each of the upper vertical members including at least one hose clip member for releasably attaching a hose to be supported.

2. The device of claim 1 wherein the at least two outwardly extending legs include a first leg assembly and a second leg assembly, each leg assembly being pivotable with respect to the base unit.

3. The device of claim 1 wherein the at least two outwardly extending legs are positionable between an extended position and a retracted position.

4. The device of claim 1 wherein the hose support assembly is pivotably engaged to the base unit.

5. The device of claim 1 wherein the hose support assembly is positionable between a vertical position and a horizontal position.

6. The device of claim 1 wherein the support arm of the hose support assembly is selectively positionable with respect to the support frame of the hose support assembly and positionable between (i) an extended vertical position and (ii) a horizontal position.

7. The device of claim 1 wherein the support arm of the hose support assembly is releasably secured to the support frame of the hose support assembly by a slidable release member that can be extended from a lower portion of the support arm and inserted into a channel defined in the support frame to thereby secure the support arm relative to the support frame.

8. The device of claim 1 wherein the telescoping assembly includes a first upper vertical member and a second upper vertical member slidably received therein.

9. The device of claim 8 wherein the telescoping assembly further includes a third upper vertical member slidably received in the second upper vertical member.

10. A collapsible and portable device for supporting a hose associated with a CPAP or BIPAP machine, the device comprising:
    a base unit having at least two outwardly extending legs;

a hose support assembly engaged to and supported on the base unit, the hose support assembly including a support frame and a support arm pivotably secured to the support frame; and a telescoping assembly of flexible upper vertical members engaged to and supported on the support arm of the hose support, each of the upper vertical members including at least one hose clip member for releasably attaching a hose to be supported;

wherein the hose support assembly is selectively positionable with respect to the base unit, and positionable between (i) an extended vertical position and (ii) a retracted position in which the hose support assembly is coplanar with the legs.

11. The device of claim 10 wherein the at least two outwardly extending legs include a first leg assembly and a second leg assembly, each leg assembly being pivotable with respect to the base unit.

12. The device of claim 10 wherein the at least two outwardly extending legs are positionable between an extended position and a retracted position.

13. The device of claim 10 wherein the hose support assembly is pivotably engaged to the base unit.

14. The device of claim 10 wherein the hose support assembly is positionable between a vertical position and a horizontal position.

15. The device of claim 10 wherein the support arm of the hose support assembly is selectively positionable with respect to the support frame of the hose support assembly and positionable between (i) an extended vertical position and (ii) a horizontal position.

16. The device of claim 10 wherein the support arm of the hose support assembly is releasably secured to the support frame of the hose support assembly by a slidable release member that can be extended from a lower portion of the support arm and inserted into a channel defined in the support frame to thereby secure the support arm relative to the support frame.

17. The device of claim 10 wherein the telescoping assembly includes a first upper vertical member and a second upper vertical member slidably received therein.

18. The device of claim 17 wherein the telescoping assembly further includes a third upper vertical member slidably received in the second upper vertical member.

* * * * *